(12) United States Patent
Bhatt et al.

(10) Patent No.: US 10,890,469 B2
(45) Date of Patent: Jan. 12, 2021

(54) METHODS AND APPARATUS FOR DETERMINING, RECOMMENDING, AND APPLYING A CALIBRATION PARAMETER FOR ACTIVITY MEASUREMENT

(71) Applicant: Under Armour, Inc., Baltimore, MD (US)

(72) Inventors: Abhi Bhatt, Austin, TX (US); Eric Boam, Austin, TX (US); Evan Torchin, Austin, TX (US); Daniel Sargeant, Austin, TX (US); Mayank Arora, Austin, TX (US); John Arnold, Jr., Austin, TX (US); John Martin, Austin, TX (US); Christopher Green, Austin, TX (US); Nimesh Desai, Austin, TX (US); Breyna Fries, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 78 days.

(21) Appl. No.: 16/390,741

(22) Filed: Apr. 22, 2019

(65) Prior Publication Data
US 2019/0242731 A1 Aug. 8, 2019

Related U.S. Application Data

(63) Continuation of application No. 15/176,599, filed on Jun. 8, 2016, now Pat. No. 10,302,469.

(51) Int. Cl.
*G01D 18/00* (2006.01)
*A61B 5/11* (2006.01)
(Continued)

(52) U.S. Cl.
CPC .............. *G01D 18/00* (2013.01); *A61B 5/112* (2013.01); *A61B 5/1112* (2013.01);
(Continued)

(58) Field of Classification Search
USPC .......................................................... 702/94
See application file for complete search history.

(56) References Cited

U.S. PATENT DOCUMENTS 7,603,255 B2 * 10/2009 Case, Jr. .................. G09B 5/02
702/182
2009/0043531 A1 2/2009 Kahn
(Continued)

*Primary Examiner* — Paul D Lee
(74) *Attorney, Agent, or Firm* — Maginot, Moore & Beck LLP

(57) ABSTRACT

Apparatus and methods are provided for determining, recommending, and applying a calibration parameter to collected activity data. In one embodiment, calibration parameter is estimated based on physical aspects of the user and automatically applied to collected data. In another embodiment, the calibration parameter is determined based on secondary data which is more precise than the data which is collected. The calibration factor based on the more precise data may comprise a recommended calibration factor, yet the user may be enabled to select any calibration factor he/she prefers via an interactive display. In one specific variant, the activity comprises a walk or run activity of the user, and the calibration parameter comprises the user's specific stride length. In another variant, the user selects a calibration factor by reviewing a list of previous activity against that same activity after calibration given a particular calibration factor is applied.

20 Claims, 7 Drawing Sheets

(51) Int. Cl.
  *A61B 5/00* (2006.01)
  *G01C 25/00* (2006.01)
  *G01C 22/00* (2006.01)

(52) U.S. Cl.
  CPC ........... *A61B 5/1118* (2013.01); *A61B 5/1121* (2013.01); *A61B 5/1123* (2013.01); *A61B 5/681* (2013.01); *A61B 5/6824* (2013.01); *A61B 5/6831* (2013.01); *A61B 5/6898* (2013.01); *A61B 5/742* (2013.01); *A61B 5/7475* (2013.01); *G01C 25/005* (2013.01); *A61B 2560/0223* (2013.01); *G01C 22/006* (2013.01)

(56) References Cited

U.S. PATENT DOCUMENTS

| | | | |
|---|---|---|---|
| 2012/0274508 A1* | 11/2012 | Brown | G04G 21/02 |
| | | | 342/357.25 |
| 2014/0129177 A1 | 5/2014 | Gyorfi | |
| 2014/0172361 A1 | 6/2014 | Chiang | |
| 2015/0141873 A1 | 5/2015 | Fei | |
| 2015/0285659 A1* | 10/2015 | Curtis | G01C 22/006 |
| | | | 702/97 |
| 2016/0007889 A1* | 1/2016 | Ananny | H04L 67/303 |
| | | | 702/104 |
| 2017/0261335 A1 | 9/2017 | Hoffman | |
| 2017/0329934 A1* | 11/2017 | Orenstein | G06Q 10/1093 |

\* cited by examiner

METHODS AND APPARATUS FOR DETERMINING, RECOMMENDING, AND APPLYING A CALIBRATION PARAMETER FOR ACTIVITY MEASUREMENT

CROSS-REFERENCE TO RELATED APPLICATIONS

This application is a continuation of U.S. patent application Ser. No. 15/176,599, filed Jun. 8, 2016, the entire contents of which are incorporated by reference herein.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

The present disclosure relates to the field of activity tracking and measurement. More particularly, the present disclosure relates to methods, devices, systems, and computer programs for determining, recommending, and applying a calibration parameter for activity measurement.

BACKGROUND

The background description provided herein is for the purpose of generally presenting the context of the disclosure. Unless otherwise indicated herein, the materials described in this or any section of the disclosure are not prior art to the claims in this application and are not admitted to be prior art by inclusion herein.

Recent advancements in electronics technology has led to the widespread use of portable devices which are able to run computer applications thereon. Accordingly, a wide variety of applications have been developed for mobile use. Among this array of recently developed mobile applications, a large number have been developed which are intended to assist a user in monitoring health-related parameters. Specifically, these applications utilize data collected by biometric monitoring devices (which may be external to the mobile device on which the application is run) to generate measurable activity logs. Such biometric monitoring devices may include, wearable devices such as heart rate monitors, nutrition trackers, smart scales, step and/or activity trackers, and others.

With respect to step and/or activity trackers, there often exists a disparity between the distance the user perceives and/or knows he/she traveled and a distance provided or calculated by the mobile application. This generally occurs when data in the wearable device contradicts global positioning (e.g., global positioning system or GPS) data, and/or the user's knowledge of distances (e.g., a normal 3 mile route). This contradiction is due in large part to the variance of each individual user's average stride length which often used as a calibration parameter for activity measurements (e.g., distance measurement). Contradictions may also be due to changes in elevation, which are unaccounted-for in traditional activity and/or step measurement systems.

Hence, what is needed is a means for determining, recommending, and applying a calibration parameter for activity measurement. Ideally, such methods and apparatus would be based on previously collected activity measurements and enable user selection and modification thereto. Apparatus and methods for accomplishing the foregoing are provided in the present disclosure.

SUMMARY OF THE DISCLOSURE

The present disclosure addresses the foregoing needs by disclosing, inter alia, methods, devices, systems, and computer programs for recommending an activity parameter.

Specifically, methods, apparatus, computer applications, and systems are provided to enable determination, recommendation, and application of a calibration parameter for measurement of an activity. In one embodiment, the determination, recommendation, and calibration are based on previously collected activity measurements and are adjustable by the user via an interactive display or interface. One specific variant, the activity comprises a walk or run activity of the user, and the calibration parameter comprises the user's specific stride length.

These and other aspects of the disclosure shall become apparent when considered in light of the disclosure provided herein.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

All Figures © Under Armour, Inc. 2016. All rights reserved.

DETAILED DESCRIPTION

Exemplary Embodiments

Disclosed embodiments include systems, apparatus, methods and storage medium associated with activity measurement calibration in general, and in particular determining, recommending, and applying a calibration parameter for activity measurement via user selection at an interactive display.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Network Architecture

Figure 1:
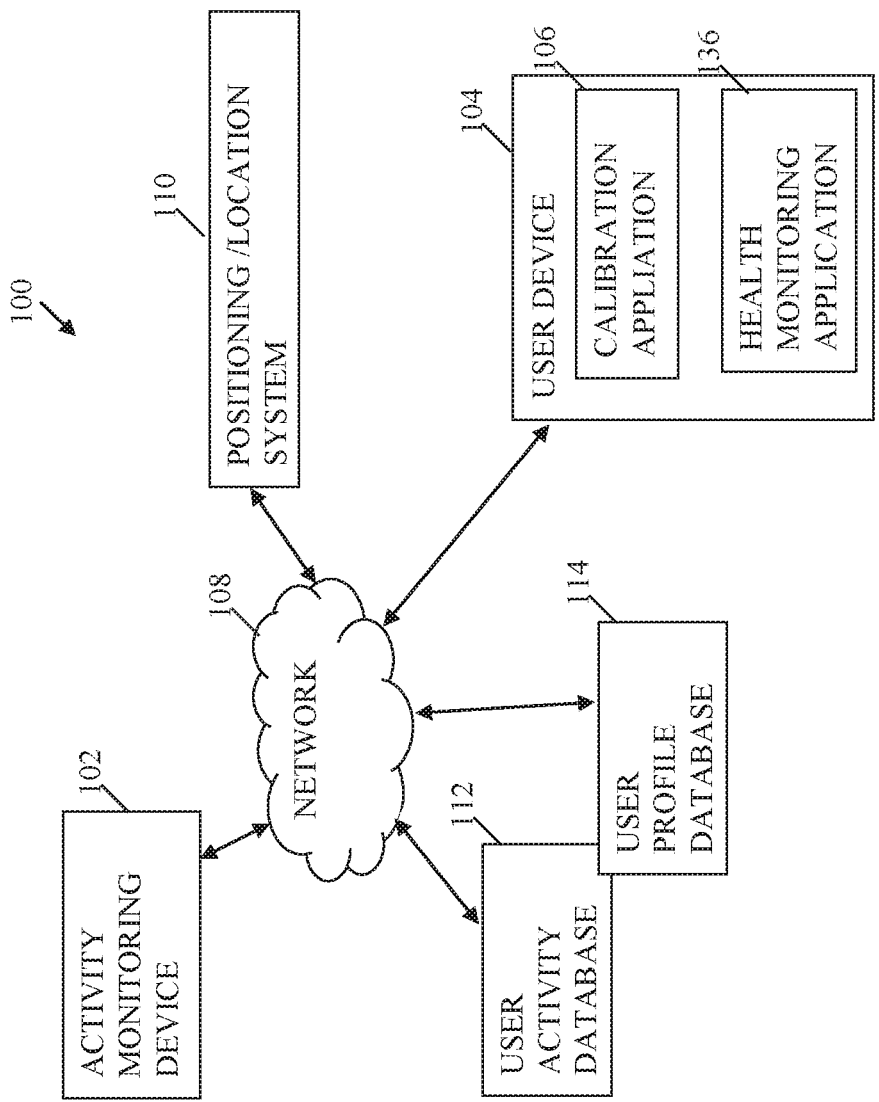
FIG. 1 is a block diagram illustrating an exemplary network for determining, recommending, and applying a calibration parameter for activity measurement in accordance with one embodiment of the present disclosure.

Referring now to FIG. 1, an exemplary network 100 for activity measurement calibration in accordance with one embodiment of the present disclosure is illustrated. As shown, the network 100 generally comprises an activity monitoring device 102 in communication with a user device 104 via a network 108. As shown, the user device 104 is generally configured to execute a calibration application 106 thereon. The calibration application 106 provides functionality to determine, recommend, and apply a calibration parameter for activity measurement in accordance with the present disclosure. In one variant, as will be discussed in greater detail elsewhere herein, the calibration application 106 comprises a suite of applications configured to cooperate to accomplish the herein disclosed functionality. The user device 104 may further communicate with a positioning/location system 110 via the network 108. Additionally, a user activity database 112 is provided in communication with the foregoing entities. It is appreciated that any number or combination of the foregoing entities may be utilized with the present disclosure, the foregoing being merely illustrative of the broader concepts. Moreover, the functionality of each of the devices discussed herein may be distributed across one or more physical entities, the configuration of FIG. 1 being one exemplary embodiment.

The activity monitoring device 102 may comprise one or more portable computing devices designed to measure, sense, monitor, or otherwise receive biometric, environmental, and/or activity parameters. In one variant, the activity monitoring device 102 comprises wearable health-related parameter measurement and computing devices, such as e.g., a smart watch, an activity tracker, a heart rate monitor, a step tracking device, smart shoe(s), and/or smart eyeglasses. In addition, an activity monitoring device 102 may comprise a smart phone having one or more of the foregoing capabilities and/or which enables manual entry of the foregoing parameters by the user thereof. The activity monitoring device 102 may process data for more than one user profile, as discussed herein.

The activity monitoring device 102 generally monitors activity of the wearer/user. For example, an activity tracking device is configured to collect activity data such as steps taken, distance traveled, rate or pace of a run, and/or flights of stairs climbed, etc.; a heart rate monitor is configured to collect heartbeat data; a step tracking device collects data relating to a number of steps taken by the user/wearer; similarly smart shoes and smart eyeglasses may collect data relating to steps, distance, pace, and/or flights of stairs climbed. Furthermore, a smart watch and/or smart phone, may be utilized as an activity tracking device, a heart rate monitor, and/or step tracking device. In one embodiment, several individual activity monitoring devices 102 may be utilized by a single user during a given activity; for example, activity data may be collected from a user's smart phone, smart shoes and step tracking band.

The user device 104 (or client device) comprises a stationary or portable computing apparatus which is configured to run a plurality of software applications thereon (as discussed in detail below) and/or access a web-based application. For example, the user device 101 may comprise a desktop computer (such as those available from Dell Computing of Austin, Tex.), or smartphone, computing tablet, laptop computer, electronic reader, personal digital assistant, and so forth. Exemplary embodiments include e.g., Galaxy S4® from Samsung Electronics of Seoul, Korea, iPhone® or iPad® from Apple Computer of Cupertino, Calif.

In one exemplary embodiment, the user device 104 runs or is configured to access (such as via a web-browser) one or more heath-monitoring applications 136 such as e.g., UA Record™, MapMyFitness®, MyFitnessPal®, Endomondo®, etc. each owned by assignee hereof. Other health activity related monitoring applications 136 may additionally be utilized in connection with the present disclosure, such as those specifically designed to receive information from a particular health monitoring device (e.g., activity monitoring device 102). For example, an application which is published by a specific sensor device 102 manufacturer may be accessed by the user device 104. The foregoing application examples are merely representative of the general concepts of the present disclosure and are not to be considered limiting to the overall scope of the disclosure.

As discussed in greater detail below, in one specific embodiment, the activity data collected by the activity monitoring device 102 comprises a step count of the user during a given workout. Generally speaking, the step count data must be processed in order to generate a measurement of the distance traveled. Processing the data may further take into account a calibration parameter which is unique to the particular user, device, and/or route. In one particular example, calibration may be performed using a user's stride length as a calibration parameter. Stride length generally refers to the distance between successive points of initial contact of the same foot. The stride length differs from person to person based on various factors including height and gait. That is, travelling a given distance for one user may require a greater or lesser number of steps than would be required for a different user to travel that same distance. Various other calibration parameters may be utilized as well. For example, calibration may comprise a percentage variance or difference such as between a known distance and a measured distance.

In one embodiment, the calibration application 106 generates a default calibration factor value for calibration of the measured activity data which is automatically applied to collected data. In a further embodiment, the calibration application 106 is configured to generate a suggested calibration factor value. The suggested or recommended value is presented to the user, who may manually elect to apply that or any other value. Derivation of the default and suggested calibration factors will be discussed in further detail elsewhere herein.

The user activity database 112 comprises one or more data stores which is configured to house information relating to the recorded activity of one or more users. In one embodiment, the user activity database 112 stores raw data having one or more identifiers associated thereto. The identifiers provide information which associates the data to e.g., a particular workout (such as by date/time), a particular user profile, a particular user device, and in some instances, to one or more particular locations (such as via additional geopositioning data). In addition or in the alternative, the database 112 may store calibrated data having metadata descriptive of a calibration factor used to generate the data. In one exemplary embodiment, as health/activity data is generated at the monitoring devices 102, it is provided simultaneously to the user activity database 112 and to the user device 102 to which the user is associated.

The user profile database 114 comprises one or more data stores which is configured to house user specific information including the user's contact information (e.g., email, geographic location, etc.), physiological parameters (e.g., gender, identity, weight, height, etc.), particular preferences (sports, celebrities/athletes, etc. of interest), goals, and other information relating to each registered user. Information specific to individual ones of a plurality of users is uniquely identified within the user activity database 112 and the user profile database 114 via a unique user profile identifier, user device 102 identifier, or other unique identifier.

The network 108 which enables communication between the one or more activity monitoring device(s) 102, user device(s) 104, user activity database(s) 112, the user profile database(s) 114, and the positioning/location system 110 may comprise a wired and/or wireless, private and/or public network, including e.g., the Internet. Accordingly, each of the one or more activity monitoring device(s) 102, user device(s) 104, user activity database(s) 112, the user profile database(s) 114, and the positioning/location system 110 is configured with appropriate networking communication interfaces (not shown). An example of wired communication interface may include, but is not limited to, Ethernet; while examples of wireless communication interfaces may include, but are not limited to, near field communication (NFC), Bluetooth, WiFi, 4G or 5G LTE. It is further appreciated that various gateways, routers, switches, based stations, and so forth may be placed between the communication interfaces of foregoing devices.

As discussed in greater detail below, derivation of a calibration factor may be based, in one embodiment, on information obtained from the positioning/location system 110. Specifically, in one embodiment, a calibration factor is determined based on a difference between a measured distance and a distance determined via position data (e.g., GPS data, GIS/map data, satellite data, etc.) from the positioning/location system 110. Hence, the system 110 itself may comprise a GPS system, GIS system, one or more satellite, one or more databases of geographic information or other information useful in providing an accurate calculation of a distance and/or position or location.

In another embodiment, the herein described functionality of the activity monitoring device 102 and the user device 104 is provided in a single device. For example, a single smart phone, smart watch, or other portable electronic device may be configured to both monitor user activity (such as via one or more sensors and/or inputs) as well as access or run a computer application configured to provide data relating to the activity to the user, e.g., a health monitoring application 136 (such as e.g., the aforementioned UA Record™, MapMyFitness®, MyFitnessPal®, Endomondo®, etc.).

In yet another embodiment, the herein described databases for storing information specific to a user (the user activity database 112 and the user profile database 114) may comprise a single database. A single user is able to link one or more health-monitoring applications such that he/she is able to sign on once and effect changes in more than one application. Such single sign on abilities and consolidated data storage are disclosed in co-owned, co-pending U.S. patent application Ser. No. 15/002,036 filed on Jan. 20, 2016 and entitled "Methods and Apparatus for Account Linking", which is incorporated herein by reference in its entirety. As discussed therein, a plurality of applications running on a user device 104 or in communication therewith are able to share data. In one exemplary embodiment, a single user device 104 is configured to run a plurality of heath-monitoring applications which collect data from a respective plurality of monitoring devices 102 and/or via user entry; once the applications are linked, the user may make updates or changes to the plurality of applications via entry thereof at a single application. Moreover, once the applications are linked, the user may sign-in to one application and be automatically signed into the other applications.

The apparatus and entities disclosed above and illustrated in FIG. 1 may be utilized for determining, recommending, and applying a calibration parameter for activity measurement consistent with the present disclosure, such as via the methods disclosed below.

Methodology

Figure 2A:
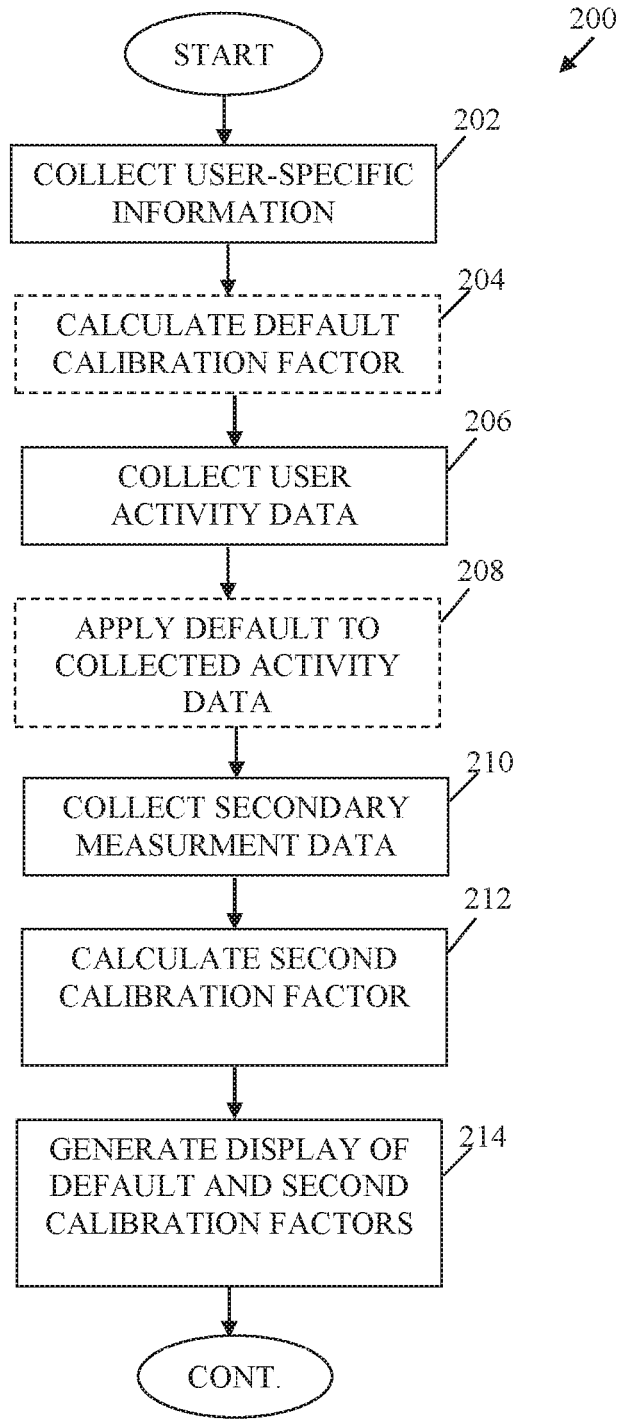
FIG. 2A is a logical flow diagram illustrating an exemplary method for determining and recommending a calibration parameter for activity measurement in accordance with one embodiment of the present disclosure.

Referring now to FIG. 2A, an exemplary method 200 for determining and recommending a calibration parameter for activity measurement is shown. Per step 202 of the method 200, user-specific information is collected. The user-specific information may comprise e.g., profile data including login identifier and password, name, age, height, weight, gender, identity, as well user preferences including sports, celebrities, and athletes of interest. The user-specific information may be collected at a user interface of the activity monitoring device 102, a user interface of the user device 104, and/or other device in communication therewith. In one embodiment, the user-specific data is stored at the user profile database 114. Storage at a centralized location such as the database 114 enables the data to be shared across multiple devices (such as the monitoring devices 102, user devices 104, and others), as noted above.

Next, at step 204, a default calibration parameter is optionally calculated. The default calibration parameter comprises an automatically determined and immediately applied calibration factor. In one embodiment, no default calibration factor is determined, and step 204 is omitted. According to this embodiment, the collected data remains uncalibrated unless a user selects to calibrate the data manually. In another embodiment, the default calibration factor may comprise an estimated stride length which is based on e.g., the user's height as determined from the user profile information of step 202. Additionally, as discussed below with regard to the exemplary user interfaces, the default calibration parameter may be displayed to the user.

At step 206, activity data is collected via an activity monitoring device 102. The activity data may comprise data relating to walking, running, rowing, cycling, or any activity involving distance including e.g., a number of steps taken, a distance traveled, an average speed, an elevation change, etc. The data may reflect a single workout or time period, such as based on a user-entered period, and a value is created for the workout period. In another variant, the data may reflect a user's entire day (e.g., 24 hrs) and therefore data may be collected throughout a day, then combined for a single value. In one embodiment, the activity data is provided to the user device 104 from the monitoring device 102 directly. Alternatively, the activity data may be provided from the activity monitoring device 102 to a user activity database 112 for centralized storage thereof. Data from multiple users is stored via a unique user and/or device 104 identifier. According to this embodiment, the user device 104 may obtain activity data from the database 112 periodically, or according to a push/pull mechanism (such as when new data is received). In yet a further embodiment, the activity monitoring device 102 may provide collected activity data to both the activity database 112 and the user device 104 simultaneously.

Per step 208, the default calibration parameter is optionally applied to the collected data. In one embodiment, as noted above, no default calibration parameter is calculated and therefore no default calibration parameter is applied (i.e., step 208 is omitted). According to this embodiment, the raw activity data may be displayed directly to the user and/or the raw activity data may be utilized in a mathematical calculation to arrive at a desired value. For example, the raw data collected may comprise a number of steps, this data may be entered into the mathematical calculation which multiplies the number of steps by the estimated stride length to arrive at a distance traveled. In another example, the raw data may comprise a series of latitude/longitude coordinates associated with particular times (i.e., waypoints in the user's activity); this data must be processed to arrive at a total distance traveled. In one implementation, the application of the default parameter occurs automatically and without user intervention. However, it is appreciated that in an alternative embodiment, the user must select the default calibration parameter in order to have it applied to the collected data. Additionally, as discussed below with regard to the exemplary user interfaces, the application of the default parameter to the data may be displayed to the user.

As noted elsewhere herein, the default calibration factor may correspond to a value which represents a physiological parameter of the user in one specific embodiment. For instance, the calibration factor may correspond to a stride length which the user takes when running or walking and the default calibration factor comprises an estimate thereof based on e.g., the user's height, weight, average or mean velocity, etc. The default calibration factor may alternatively correspond to a numerical value or multiplier, such as occurs when e.g., uncalibrated distance data is simply received from the activity monitoring device 102; a calibration factor of 1 is used to result in data that remains uncalibrated. Other exemplary default calibration parameters are discussed in greater detail elsewhere herein.

At step 210, secondary measurement data is collected relating to the recommended calibration determination. Specifically, in one embodiment, the secondary measurement data comprises data obtained via consultation with the positioning/location system 110. That is, information may be collected from the positioning/location system 110 which identifies a precise geographic location of the activity monitoring device 102 as it monitors user activity (e.g., such as during a workout and/or during a 24 hr period). The collection/generation of geographic information is discussed elsewhere herein. The geographic information is utilized to determine e.g., a distance traveled, elevation change during the user's activity, as discussed elsewhere herein.

Next, per step 212, a second calibration factor is calculated. In one embodiment, the second calibration factor is mathematically determined to, when applied to collected activity data, result in more accurate activity measurements than the default factor and/or no calibration factor and is referred to as a "recommended" or "suggested" calibration factor. Stated differently, the recommended calibration factor corrects the data by an amount or multiplier which the data was "off". In one specific embodiment, the recommended calibration factor comprises a relationship (e.g., ratio) between collected distance data to a distance determined using geo-position data. In another specific embodiment, the recommended calibration parameter comprises a recommended stride length which is determined by comparing a distance derived using an estimated stride length to a distance derived from geo-position data (e.g., map data). In yet another embodiment, the recommended calibration factor comprises a value by which the collected data should be reduced or increased in order to arrive at the next nearest milestone distance (e.g., quarter mile, half mile, etc.); in other words, the amount needed to round up or round down the collected data to a next nearest e.g., quarter mile. These and other recommended or suggested calibration parameters may be used with the present disclosure, the foregoing being merely exemplary of the underlying principles of the disclosure.

Finally, per step 214, the default and second calibration factors are displayed to the user. As discussed below with regard to the exemplary user interfaces, the calibration factors may be identified to the user in an interactive display. In one embodiment, the interactive display on which the calibration factors are displayed is further configured to enable the user to adjust the calibration manually.

Figure 2B:
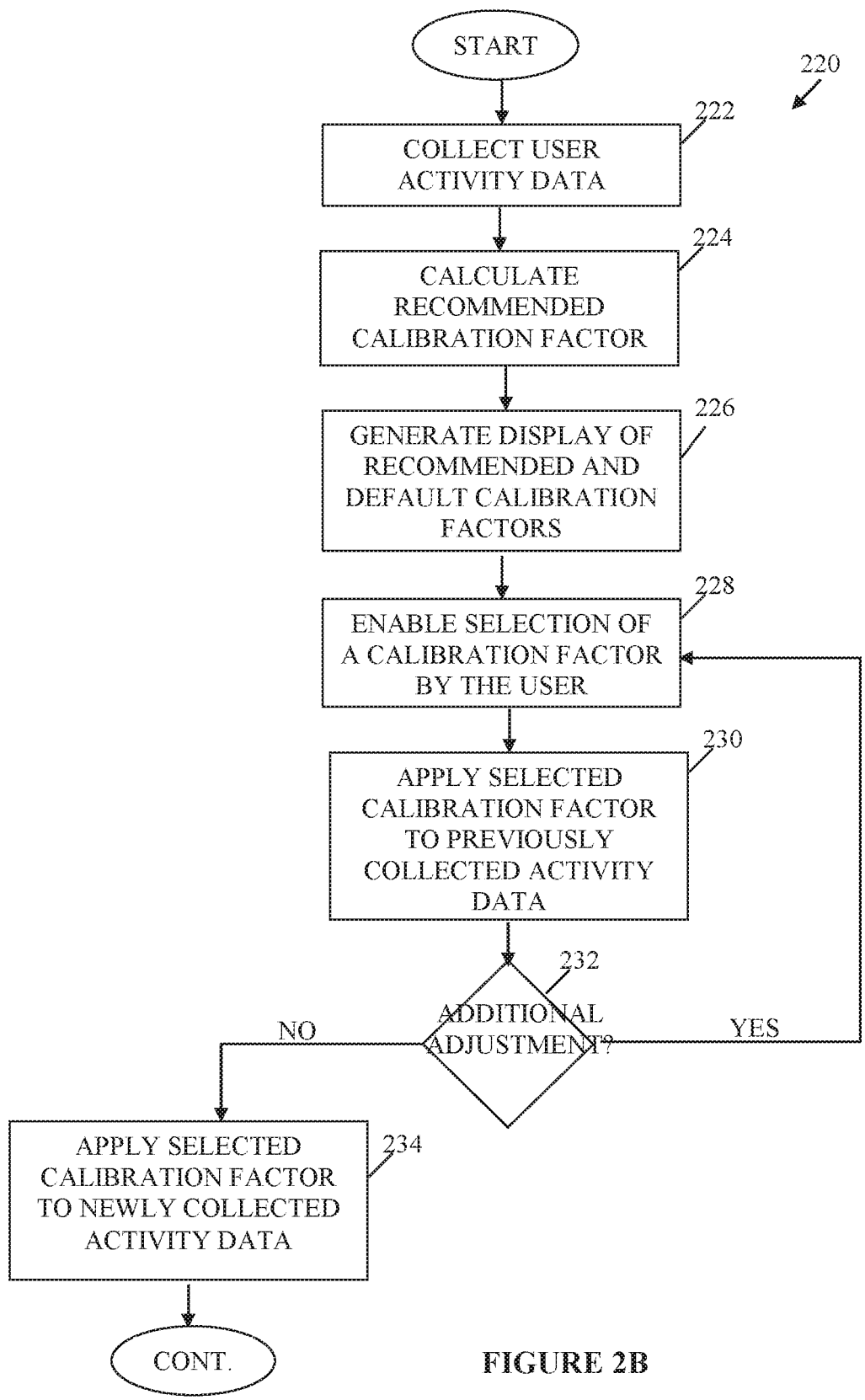
FIG. 2B is a logical flow diagram illustrating an exemplary method for applying a calibration parameter for activity measurement in accordance with another embodiment of the present disclosure.

Referring now to FIG. 2B, a detailed method 220 for applying a calibration parameter for activity measurement is given. As shown, per step 222, activity data is collected from the monitoring device 102 (and/or at the activity database 112) at a user device 104. The activity data may comprise e.g., step count, distance traveled using GPS data, accelerometer data, etc.

Next, at step 224, a recommended calibration factor is calculated. In the instance that the recommended calibration factor relates to a recommended stride length, the calculation may be based on a comparison of the number of steps taken and the actual distance traveled (determined via geoposition data associated to the collected activity data). Specifically, the number of steps taken is multiplied by the estimated stride length to arrive at a first distance; then, the first distance is compared to other distance data (such as collected from map data, GPS data or the like). The recommended calibration factor or stride length in this instance, would comprise the stride length needed which when multiplied by the number of steps to result in the geoposition-determined distance. In another alternative, the recommended calibration factor may comprise a number or a multiplier by which the measured distance traveled must be added, subtracted or multiplied to arrive at a calibrated distance. In one variant, the calibrated distance comprises an independently measured distance traveled by the user.

In another example the measured distance is determined via less precise distance measurement systems such as by using GPS data. According to this variant, the calibrated distance is determined from a precise distance measurement such as e.g., map data. Then, as noted, these are compared and a recommended calibration factor is determined as an amount (whether a multiplier or addition/subtraction), needed to align the measured distance to the actual distance.

At step 226, the recommended and default calibration parameters are displayed to the user via a graphic user interface (GUI). The GUI, in one variant, comprises a field in which the user may enter a calibration factor in the form of a number; the default and/or recommended calibration factor are listed in a non-editable portion of the screen. In another embodiment, the GUI comprises a sliding bar, ruler, or other visual guide on which a marker for the default calibration factor and/or a marker for the recommended calibration factor are displayed.

Next, at step 228, the user is provided with a mechanism to select a calibration factor via the GUI. The user may consult the displayed recommended and/or the default calibration parameters when selecting a calibration factor. Via the previously referenced entry field, the user may manually enter a number as the calibration factor such as using a keyboard (including e.g. a touch screen keyboard). The slidable (e.g., bar, ruler or guide) display may be automatically set to the default number (or the whole number 1 in the instance no calibration is to be applied), and the recommended calibration factor may also be identified on the display. According to this embodiment, the user may slide the bar, ruler, or guide using e.g., a touch screen of the user's device (e.g., user device 104), a mouse, or other device or mechanism. In this manner, the user may slide the display e.g., toward the recommended factor and thereafter the default factor remains identified on the slidable display. As the user moves position indicator to a position distinct from both the recommended and default calibration parameter, both of these may be indicated on the slidable display. These and other features of the interactive display will be discussed in detail below. It is further appreciated that each of the foregoing features of the GUI may be utilized in conjunction with one another and are not intended as exclusive options; that is, in one embodiment the slider bar includes a filed in which the user may manually enter a number for the calibration factor.

At step 230, the selected calibration actor is applied to previously collected data. In other words, in one embodiment, a portion of the display includes a list of previously recorded activity entries from the user's activity monitoring device 104. When the user selects a calibration factor, it is applied to the previously collected data such that a newly calibrated amount for each of the list of previously recorded activity entries is displayed alongside the uncalibrated data (and/or data to which the default calibration parameter is applied). In one variant, the list of previously recorded activity entries and the newly calibrated list of previously recorded activity entries are displayed in close proximity to one another, so that the user may review the changes and determine whether further manipulation to the calibration factor is needed (step 232).

When it is determined at step 232 that further calibration is needed, the process 200 repeats to step 228 wherein the user is able to select another calibration factor (such as by manipulation of the slider and/or manual entry thereof). Per step 230 the newly selected calibration factor is applied to the previously collected activity data as discussed above. The selection and application of calibration parameters occurs in repetition until the user determines that no further manipulation or adjustment is needed.

When it is determined at step 232 that further calibration is not needed, the selected calibration factor is stored and when subsequent activity data is collected relating to the user, the stored/saved calibration factor is applied thereto (step 234). In one embodiment, the selected calibration factor is stored at the user device 102; when additional data is collected, the stored calibration factor is accessed and applied. When the user selects a different calibration factor, the first selected factor is deleted or erased such that only the most recently selected calibration factor is stored in one embodiment.

Figure 2C:
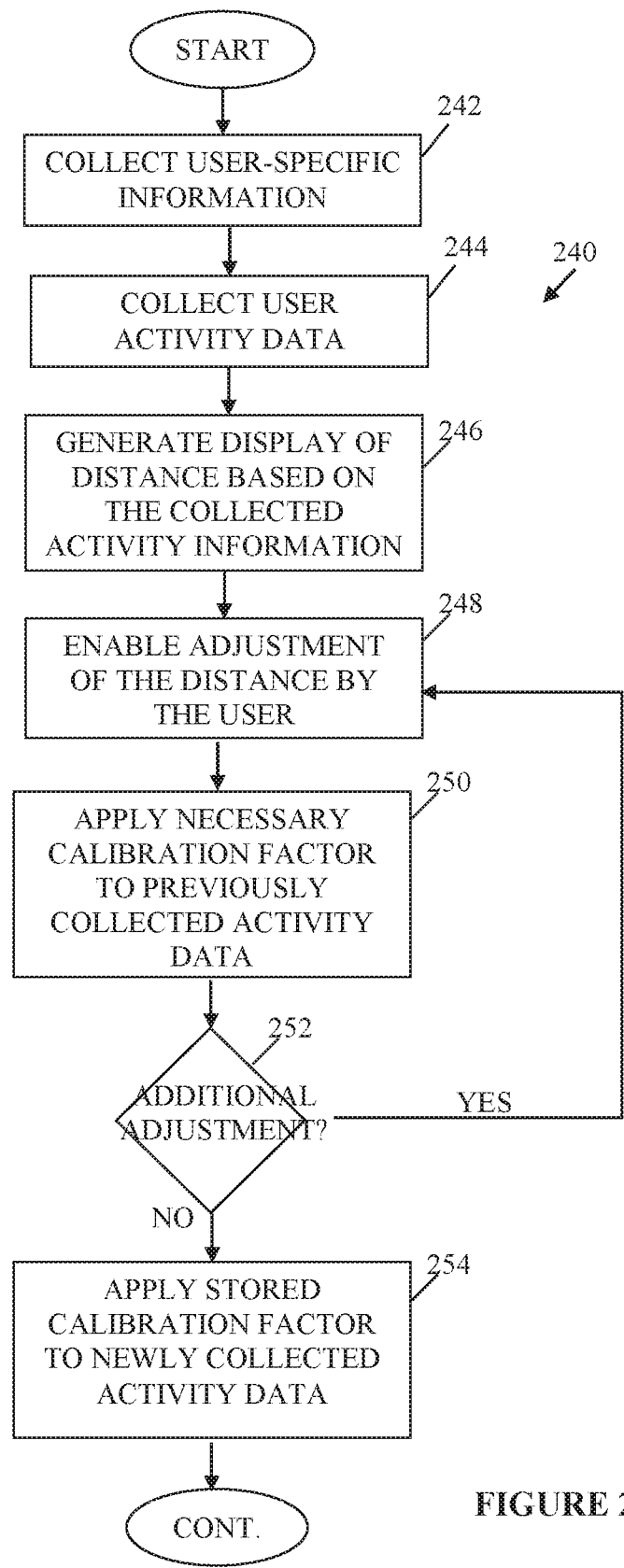
FIG. 2C is a block diagram illustrating a second exemplary method for applying a calibration parameter for activity measurement in accordance with one embodiment of the present disclosure.

Referring now to FIG. 2C a second exemplary method 240 for applying a calibration parameter for activity measurement is illustrated. As shown, per step 242 information is collected relating specifically to the user. For example, user profile information may include: name, user identifier, password, gender, identity, height, weight, etc. This information may be stored at the device 102, the monitoring device 104 and/or the user profile database 114. Next, at step 244, user activity data is collected. The user activity data in one embodiment may comprise a step count, accelerometer data, GPS data, and/or other sensor data. The user activity data is received from a monitoring device 102 and may be sent directly to the user device 104 or alternatively may be routed through an activity database 112.

Similar to the methods discussed above, per step 246, a distance is generated based on the collected activity information and displayed. In one embodiment, the distance is uncalibrated and/or displayed as collected (i.e., raw data). Such is the case when the collected data comprises GPS data, for example. In another embodiment, the distance is calibrated according to a default calibration parameter. For example, distance may be derived by multiplying the collected step data by an estimated stride length (derived based on height).

Next, at step 248, the user is provided with a mechanism by which he/she may adjust the distance. In one example, assume that the collected data reflects a distance of 3.13 miles however the user knows or is otherwise aware that the real distance traveled comprises precisely 3.00 miles. For example, he/she may have run or walked on a track, or on a marked and measured trail. The mechanism by which the user adjusts the distance may comprise a field in which the user manually enters a distance (e.g., 3.00). In another embodiment, the mechanism may comprise a slider bar and an indicator on the slider may be moved by the user (via touch, mouse, etc.) such that when the user stops or pauses on the slider, the number at which the indicator is pointed is utilized as a calibration factor and the distance data is updated accordingly. Accordingly, at step 250, a necessary calibration factor is applied to the previously collected activity data based on the user's adjustment (step 248). In other words, when the user adjusts the distance data a calibration factor representative of the adjustment is applied to the previously collected data, and a newly calibrated amount for each of the list of previously recorded activity entries is displayed alongside the uncalibrated data. In one variant, the list of previously recorded activity entries and the calibrated list of previously recorded activity entries are displayed in close proximity to one another, so that the user may review the changes and determine whether further adjustment to the distance is needed (step 252).

When it is determined at step 252 that further calibration is needed, the process 200 repeats to step 248 wherein the user is able to continue to adjust the distance (such as by manipulation of the slider and/or manual entry thereof). Per step 250 the newly adjusted distance causes generation of a new calibration factor which is applied to the previously collected activity data as discussed above. The selection and application of calibration parameters occurs in repetition until the user determines that no further manipulation is needed.

When it is determined at step 252 that further adjustments are not needed, the selected calibration factor is stored and when subsequent activity data is collected relating to the user, the stored/saved calibration factor is applied thereto (step 254). In one embodiment, the selected calibration factor is stored at the user device 102; when additional data is collected, the stored calibration factor is accessed and applied. When the user causes a different calibration factor to be derived (via manipulation of the distance of at least one previous activity data entry), the first factor is deleted or erased such that only the most recently selected calibration factor is stored.

The methods disclosed above and illustrated in FIGS. 2A-2C may be implemented in one embodiment by a user device 102, such as that disclosed below.

Exemplary User Device

Figure 3:
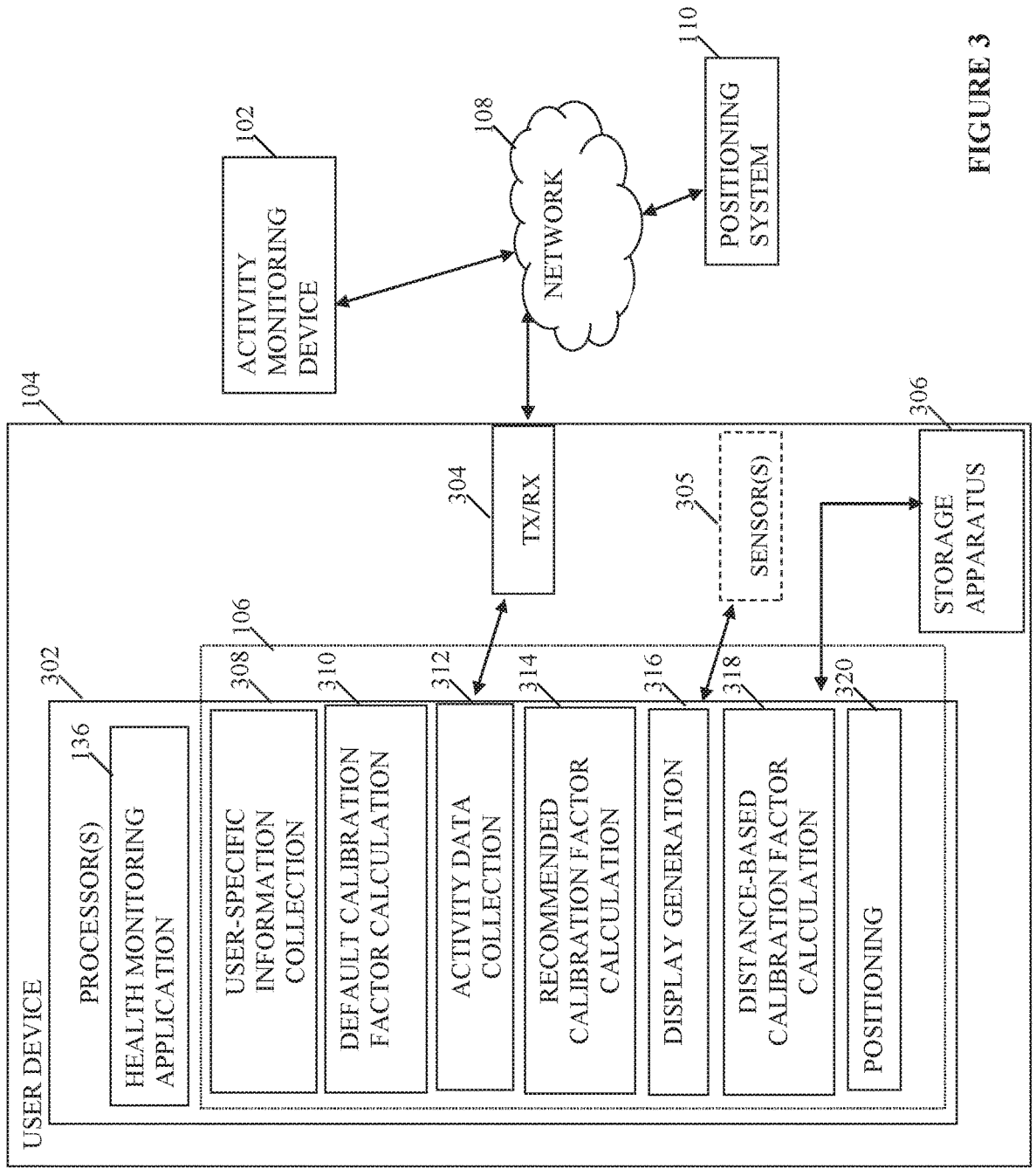
FIG. 3 is a block diagram illustrating an exemplary user device configuration in accordance with one embodiment of the present disclosure.

Referring now to FIG. 3, an exemplary user device 104 is provided. The user device 104 may comprise a portable computerized device in one particular embodiment. As illustrated, the device 104 comprises a processor 302, a transceiver 304, and a storage device 306. As discussed in further detail below, the processor 302 is operable to run at least one health and/or activity monitoring application 136 and at least one calibration application 106 thereon. Alternatively, the device 104 may access remotely stored applications (such as application 136 and/or 106) via a web browser or other network interface.

In another embodiment, the user device 104 may comprise one or more optional sensors 305. Such is the case e.g., in the instance the user device 104 comprises functionality of at least one of the activity monitoring devices 102. For example, the user device 104 may comprise a smart phone, smart watch, or other portable electronic device that is configured to both monitor user activity (such as via one or more sensors and/or inputs; not shown) as well as to access or run a computer application configured to provide data relating to the activity to the user e.g., a health monitoring application 136.

The transceiver 304 of the exemplary user device 104 illustrated in FIG. 3 enables receipt and transmission of communications to and from the user device 104. For example, the transceiver 304 facilitates the transmission of user activity updates and/or profile updates entered at the user device 104 to the appropriate database (e.g., the user activity database 112, the user profile database 114, etc.); the transceiver 304 is also configured to receive sensed/measured/obtained raw data from various sensors at the monitoring devices 102. In addition, the transceiver facilitates transmission of location-related information between the device 102 and a positioning/location system 110. Still further, the transceiver 304 enables the device 104 to communicate calibrated user activity data to the activity database 112.

The storage apparatus 306 of the exemplary user device 104 in FIG. 3 is configured to store local copies of e.g., collected raw activity data (received from the monitoring devices 102), a most recently selected calibration parameter, a client-side version of the aforementioned computer applications (e.g., the calibration application 106 and the health monitoring application 136), and any other locally created or stored data.

As noted above, the processor 302 is configured to execute at least a health monitoring application 136 and a calibration application 106 thereon. In one embodiment, however, it is noted that the functionality of these applications may be combined into a single user-facing application. That is, the user may access the functionality of both by launching a single application and using a single interface.

The health monitoring application 136 comprises a plurality of instructions which are configured to provide a user with display and/or analysis of data measured, collected, sensed, monitored, or otherwise received at the device 104 (including received from other monitoring devices 102 and/or a sensor apparatus of the device 104 itself). Exemplary health monitoring applications 136 include e.g., UA Record™, MapMyFitness®, MyFitnessPal®, Endomondo®, etc. each owned by assignee hereof. Other health activity related monitoring applications 136 may comprise those specifically designed to receive information from a particular health monitoring device (e.g., activity monitoring device 102). For example, an application which is published by a specific sensor device manufacturer may be accessed by the user device 104. In one embodiment, the data which is displayed and/or analyzed by the health monitoring application 136 is first calibrated using the calibration application 106 discussed elsewhere herein. Other specific functions of the health monitoring application 136 are outside the scope of the present application and therefore will not be discussed herein.

The calibration application 106 comprises a plurality of instructions which are configured to enable calibration of data received at the user device 104 (such as from the activity monitoring device(s) 102) to a particular user. Specifically, the embodiment of the calibration application 106 of FIG. 3 comprises a suite of applications including: a user specific information collection application 308, a default calibration parameter calculation application 310, an activity data collection application 312, a recommended calibration parameter calculation application 314, a display generation application 316, a distance-based calibration factor calculation application 318, and a positioning application 320. Each of these sub-applications within the calibration application 106 suite will be discussed in turn below; it is also appreciated that the herein disclosed functionality may be split between as many or as few individual applications as desired consistent with the present disclosure.

The user specific information collection application 308 comprises a plurality of instructions which are configured to enable collection of information relating to the user, such as username, password, sports and celebrity interests, gender, identity, height, weight, age, etc. In one embodiment, the application 308 may cause presentation of an interface to the user in which he/she may enter certain details relating to his/her personal attributes. In another alternative, the data is entered at a separate device (such as e.g., a monitoring device 102), and thereafter provided to the collection application 308 of the user device 104 directly and/or via the user profile database 114.

The activity data collection application 312 comprises a plurality of instructions which are configured to enable collection of activity data relating to the user, such as workout data, daily steps taken, sleep data, etc. The data is collected from the one or more sensors 305 and/or the sensors of one or more monitoring devices 102 in communication therewith. The data collection application 312 may determine a timeline for when data is to be collected, such as e.g., daily, twice daily, after the user signals the beginning and/or ending of a workout, etc.

The positioning application 320 comprises a plurality of instructions which are configured to enable communication of information between the device 104 and a positioning/location system 110. For example, the device may transmit a signal which is received at the positioning/location system 110 and which enables the system 110 to determine a precise geographic location of the device 104. As will be discussed in greater detail below, determination of a precise geographic location of the device 104 may be utilized to determine e.g., a distance traveled during the user's activity. In another embodiment, the activity monitoring device 102 transmits signals to the positioning/location system 110 which then determines a precise position of the monitoring device 102 (such as during a workout). The determined position may be provided to the user device 104 (and also to the monitoring device 102), which via the positioning application 320 assigns the position data to activity data received from the monitoring device 102. In other words, as activity data is received from the activity monitoring device 102, it is associated with one or more geographic locations/positions received from the positioning/location system 110 via the positioning application 320.

The default calibration parameter calculation application 310 comprises a plurality of instructions which are configured to enable generation of a default calibration factor which is immediately and automatically applied to collected data, i.e., a default calibration factor. In one embodiment, the default calibration factor is set to a multiplier of 1, i.e., no calibration. In another embodiment, the default calibration factor corresponds to a value which represents a physiological parameter of the user. For example, the calibration factor may correspond to a stride length which the user takes when running or walking, as discussed above. In this example, the default calibration factor may be set to an estimated stride length for the user. The estimate may be based on e.g., the user's height, weight, average or mean velocity, etc. The default calibration parameter calculation application 310 is further enabled to, when the default calibration factor is determined, calculate a calibrated value for one or more previously collected data values, as will be illustrated elsewhere herein. In this manner, the user may review calibrated figures upon selection of a calibration factor to determine whether further modification of the calibration factor is needed.

The recommended calibration parameter calculation application 314 comprises a plurality of instructions which are configured to enable generation of a calibration factor which is mathematically determined to, when applied to collected activity data, result in more accurate activity measurements than the default factor and/or no calibration factor, i.e., a recommended or suggested calibration parameter. In one embodiment, the recommended calibration factor corresponds to a multiplier which represents an amount or value by which collected data is "off". For example, suppose it is determined (such as via the mechanisms discussed elsewhere herein) that the collected data of a 1.75 mile run actually corresponds to a 2.19 mile run (as determined from geopositioning data). Accordingly, the distance is determined to be "off" by a factor of 1.25; this number is the recommended calibration factor. In another embodiment, the recommended calibration factor may comprise a recommended stride length based on e.g., a comparison of a number of steps taken and a distance traveled (determined by the aforementioned positioning application 320), as discussed elsewhere herein. In yet another embodiment, the recommended calibration factor comprises a value by which the collected data should be reduced or increased in order to arrive at the next nearest quarter mile (0.25). For example, suppose a particular run is measured (un-calibrated) as 1.33 miles, the recommended calibration factor generation application 314 determines that 1.33 miles is 0.08 miles more than 1.25 miles and 0.17 miles less than 1.50 miles. Since the un-calibrated number is closer to 1.25 miles than to 1.50 miles, the recommended calibration factor generation application elects –0.08 as the recommended calibration factor.

The recommended calibration parameter calculation application 314 is further enabled to, when a user saves entry of a calibration factor, calculate a calibrated value for one or more previously collected data values, as will be illustrated elsewhere herein. In this manner, the user may review calibrated figures upon selection of a calibration factor to determine whether further modification of the calibration factor is needed.

The distance-based calibration factor calculation application 318 comprises a plurality of instructions which are configured to enable generation of a calibration factor which corresponds mathematically to a difference or ratio between a measured distance and a user-entered distance. For example, assume that the measured distance comprises 3.13 and the user-entered distance for the same activity comprises 3.00 miles. The distance-based calibration factor calculation application 318 determines a relationship between 3.13 miles and 3.00 miles (i.e., the calibration factor). Finally, when a user saves entry of a the distance, the resultant calibration factor is saved and used to calculate a calibrated value for one or more previously collected data values, as will be illustrated elsewhere herein. In this manner, the user may review calibrated figures upon selection of a calibration factor to determine whether further modification of the calibration factor is needed.

The display generation application 316 comprises a plurality of instructions which are configured to enable generation of a plurality of user interfaces discussed herein. Specifically, one or more user interfaces may be generated which enable the user to: enter user-specific information;

review previously collected activity data; review a list of activity data which is calibrated using a default calibration factor; enter or adjust a calibration factor; review a list of activity data which is calibrated using a recommended calibration factor; and identify a default and/or recommended calibration factor on a measurement device (such as a slider or ruler). These and other features of the exemplary interfaces will be discussed in further detail below with regard to FIGS. 4A, 4B, and 4C.

It is appreciated that the user device 104 may comprise additional applications which contribute to the functioning thereof as described herein and/or the foregoing functionality may be distributed across more applications or combined into fewer applications. For example, the aforementioned health monitoring may be provided via a separate application not discussed herein for ease of understanding. These and other necessary components of the user device 104 will be clear to a person of ordinary skill in the art given the discussion of the functionality herein.

In one embodiment, the aforementioned processing is performed via coordination of a distributed application having client and network-side components. The network-side component may be run at a network entity and the client-side component run at the user device 104.

The herein-described applications which enable the calibration functionality discussed throughout the disclosure include e.g., the user specific information collection application 308, the default calibration parameter calculation application 310, the activity data collection application 312, the recommended calibration parameter calculation application 314, the display generation application 316, the distance-based calibration factor calculation application 318, and the positioning application 320. A permanent copy of the programming instructions for these applications (308, 310, 312, 314, 316, 318, and 320) may be placed into permanent storage devices (such as e.g., the storage apparatus 306) during manufacture of the user device 104, or in the field, through e.g., a distribution medium (not shown), such as a compact disc (CD), or from a distribution server (not shown) via the network 108. That is, one or more distribution media having an implementation of the agent program may be employed to distribute the agent and program various computing devices.

The herein described calibration applications (308, 310, 312, 314, 316, 318, and 320) improve the functioning of the user device 104 by enabling it to provide a means by which the user may easily adjust a calibration parameter to cause collected data to more accurately represent the measured activity. Furthermore, devices that are able to provide a mechanism for calibration adjustment as disclosed herein can operate more efficiently to provide accurate distance measurements which meet a user's standard which assists the user in viewing health-parameter data and establishing and maintaining healthy lifestyle patterns.

Exemplary User Interfaces

Figures 4A, 4B:
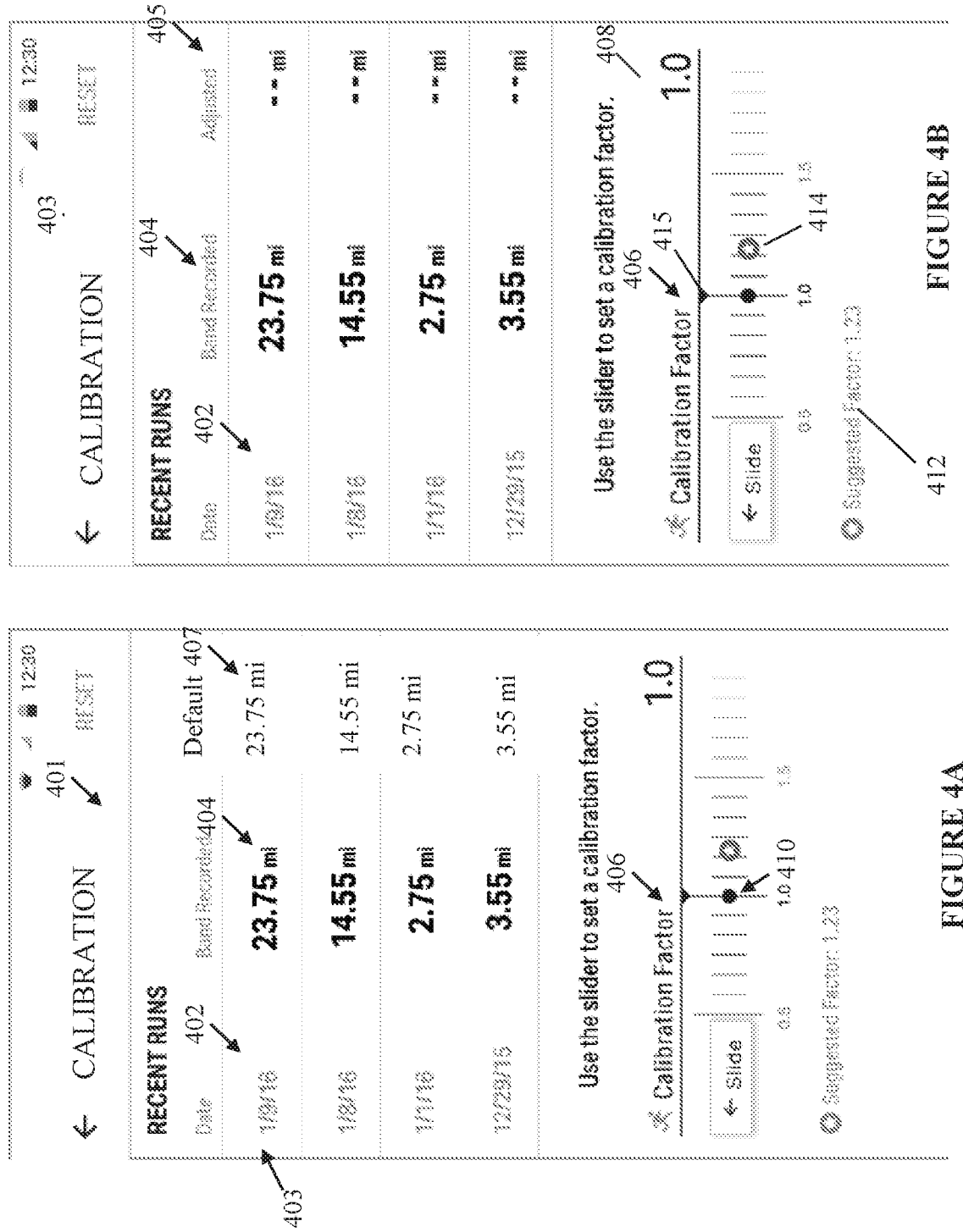
FIG. 4A is a diagram illustrating an exemplary user interface demonstrating the utilization of a default calibration parameter and the recommendation of a calibration parameter for activity measurement in accordance with one embodiment of the present disclosure.
FIG. 4B is a diagram illustrating an exemplary user interface demonstrating the selection of a calibration parameter for activity measurement in accordance with one embodiment of the present disclosure.

Referring now to FIG. 4A, an exemplary user interface 401 demonstrating the utilization of a default calibration parameter and the recommendation of a calibration parameter for activity measurement is illustrated. As shown, the interface 401 provides a list of recent activity listed from most to least recent by date 402. In the illustrated embodiment, only the four most recent runs are shown, but it is appreciated that any type of activity involving distance (such as walking, cycling, rowing, etc.) may be measured; additionally, any number of recent activity entries may be listed. The illustrated embodiment is merely exemplary of the overall concepts of the disclosure.

As shown, for each entry 403 in the list, a date 402, measured distance 404, and default calibrated distance 407 is given. In the illustrated embodiment, the default calibration parameter is demarked by a solid dot 410 on the calibration factor sliding scale 406 at the lower portion of the interface 401. In the given example, the default calibration factor is immediately applied to the collected data. In this case, the default parameter of 1.0 is applied, resulting in default distances 407 which match the recorded distances 404 (i.e., n×1=n). However, it is appreciated that in another embodiment, no default calibration parameter is utilized. In yet another embodiment, the recorded distances 404 may be pre-calibrated using the default calibration factor and simply presented to the user as a recorded distances such as in the example of FIG. 4B.

Also illustrated in the interface 403 of FIG. 4B, is a suggested calibration factor which is demarked by a dot having a star in its center 414. The suggested factor may also be listed at the bottom of the interface 412, below the slider 406. As noted elsewhere herein, the slider functions by enabling a user to touch anywhere on slider and move his/her finger right or left in order to move the indicator 415 to a different location on the slider 406. As the user moves the indicator 412 away from the default position 410, the recorded distances 404 are adjusted to give newly calibrated distances 405. Additionally, as the user slides the indicator 415 the current calibration factor 408 is provided just above the slider 406. Hence as the user moves his position the current factor 408 adjusts accordingly. When the user pauses at a given position for a predetermined period of time, the recorded distances are adjusted to create adjusted or calibrated distances 405. In another embodiment, the user may simply touch either instance of the suggested factor to have the indicator 415 immediately relocate (or "snap") to the position of that calibration factor on the slider 406.

It is further appreciated, that in another embodiment, a speed at which the ruler 406 is moved may vary based on the user's movement. In other words, as the user scrolls left or right faster, the distance between any two whole numbers may shorten. Moreover, as the user scrolls left or right more slowly, the distance between any two whole numbers may increase; i.e., more tic-marks or fractions of whole numbers may appear as stopping places. In yet another embodiment, the slider 406 provides a mechanism whereby the user may press and hold the ruler/slider 406 in order for an expanded view of the ruler to be presented. The user may then work within the expanded view to select a point which he/she feels provides the most accurately calibrated data.

Figure 4C:
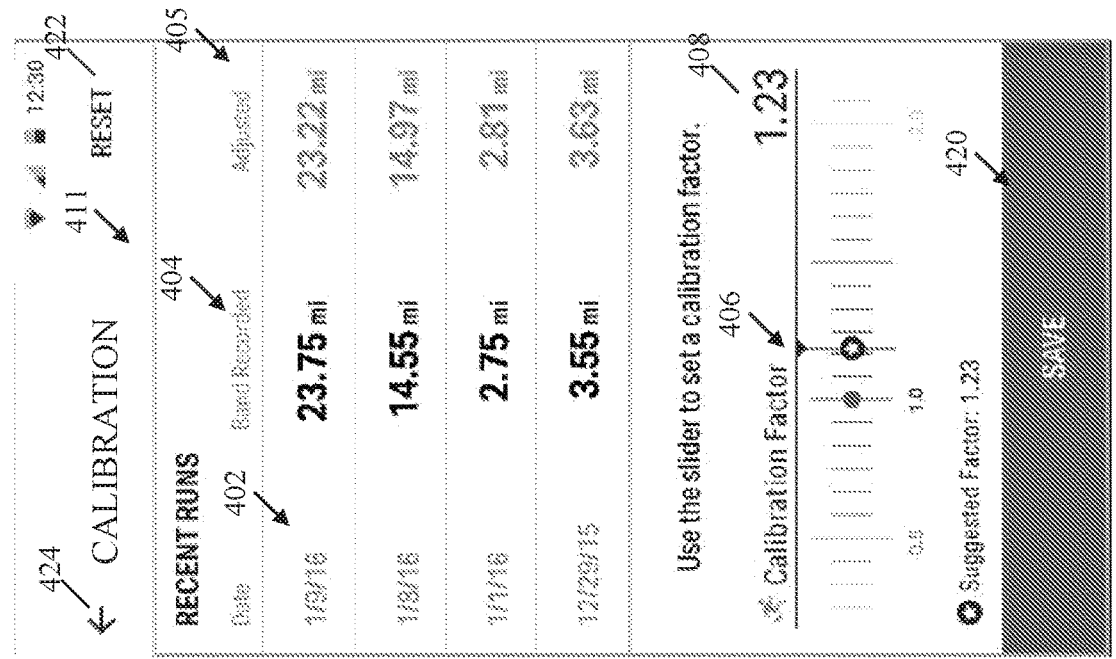
FIG. 4C is a diagram illustrating an exemplary user interface demonstrating the application of the selected a calibration parameter to past activities in accordance with one embodiment of the present disclosure.

Referring now to FIG. 4C, an exemplary user interface 411 demonstrating the application of the selected a calibration parameter to past activities is illustrated. As shown, once the user has selected a calibration factor amount it is displayed as the current calibration factor 408, and applied to the recorded values 404 to arrive at adjusted values 405. In the example of FIG. 4C, the user has selected the suggested factor 412 as the calibration factor 408, however it is appreciated that the user may select any number of calibration factors, the foregoing being merely exemplary. Once the user has selected the calibration factor, the amount may be saved (such as to the device 102 storage 306) via the user's selection of the 'save' button 420.

Also illustrated in the user interface 411 of FIG. 4C, are a reset button 422 and a return button 424. In one embodiment, the reset button 422 may restore the interface to the default calibration interface (such as interface 401 of FIG. 4A). The user may select this option when he/she is unhappy with his/her current calibration selection and would like to begin the process of determining a workable calibration factor again. The return button 424 enables the user to return to the previous screen without saving the current calibration factor 408. In one embodiment, before either the reset and/or return functions are implemented, the user may be prompted to verify that they wish to proceed without saving the current calibration factor 408.

Although not illustrated, it is further appreciated that the foregoing interfaces may further provide a mechanism for the manual entry of a calibration factor and/or distance (as noted above). In the instance the user manually enters a calibration factor, it is further appreciated that in one embodiment, this may cause the indicator 415 to immediately relocate (or "snap") to the position of that calibration factor on the slider 406. Moreover, in the instance the user manually enters a distance, the indicator 415 may immediately relocate (or "snap") to a position of an appropriate calibration factor to arrive at the user-entered distance given the uncalibrated data (as noted elsewhere herein).

In summary, a method of determining a recommended a calibration parameter for measurement of a user's activity is disclosed. In one embodiment, the method comprises: (i) collecting a plurality of data relating to said user's activity; (ii) applying said default calibration parameter to said plurality of data relating to said user's activity to generate a measurement of said user's activity; (iii) collecting a plurality of secondary data relating to said user's activity; and (iv) utilizing said plurality of secondary data to calculate a recommended calibration parameter for measurement of said user's activity.

In addition, system configured to determine a recommended a calibration parameter for measurement of a user's activity is disclosed. In one embodiment, the system comprises: a positioning system; at least one activity monitor; and at least one user device, said user device configured to: (i) receive an input by said user of said user's height; (ii) utilize said height to estimate a stride length of said user; (iii) receive a step count of said user during at least one first activity from said at least one activity monitor; (iv) receive position data of said user during said at least one first activity from said positioning system; (v) utilize said step count and said position data to determine a recommended stride length of said user; and (vi) display said estimated stride length and said determined recommended stride length to said user.

Furthermore, a non-transitory, computer readable medium is disclosed. In one embodiment, the non-transitory, computer readable medium comprises a plurality of instructions which are configured to, when executed: (i) receive an input by a user of at least one user parameter used in calibration; (ii) utilize said at least one user parameter to estimate a calibration of activity data of said user; (iii) receive data relating to at least one first activity of said user; (iv) receive position data of said user during said at least one first activity; and (v) utilize said data relating to said at least one first activity of said user and said position data to determine a recommended calibration.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method of determining a recommended calibration parameter for measurement of a user's activity, said method comprising:
   collecting a first plurality of data relating to a user's activity from at least one sensor disposed in a shoe worn by the user during said user's activity;
   generating a default calibration parameter for said user based on user profile data;
   generating first activity data by applying said default calibration parameter to said first plurality of data;
   displaying said first activity data via a display apparatus;
   collecting a second plurality of data relating to said user's activity from at least one sensor disposed in a mobile device worn or carried by the user during the user's activity;
   utilizing said second plurality of data to calculate a recommended calibration parameter for measurement of said user's activity;
   displaying on an interactive display an identifier relating to said recommended calibration parameter;
   enabling said user to select a current calibration parameter from said display; and
   displaying second activity data using said user-selected current calibration parameter.

2. The method of claim 1 further comprising, prior to displaying said second activity data, generating the second activity data by applying said user-selected current calibration parameter to said first plurality of data.

3. The method of claim 1, wherein the second plurality of data relating to said user's activity comprises global positioning satellite (GPS) data, and wherein said recommended calibration parameter is based on a total distance traveled as determined from said GPS data.

4. The method of claim 1, wherein said user's activity comprises a walking, running, cycling, and/or rowing activity for a distance.

5. The method of claim 1, wherein said interactive display includes a scale, wherein said default calibration parameter and said current calibration parameter are simultaneously displayed on said scale.

6. The method of claim 1, wherein said interactive display includes a scale, wherein said identifier relating to said recommended calibration parameter is a first identifier, the method further comprising:
   displaying a second identifier relating to said current calibration parameter on said scale prior to enabling said user to select said current calibration parameter from said display.

7. The method of claim 6 wherein the first identifier is stationary relative to said scale, wherein said second identifier is moveable relative to said scale, and wherein enabling said user to select said current calibration parameter includes enabling said user to move said second identifier relative to said scale.

8. A method of determining a recommended calibration parameter for measurement of a user's activity, said method comprising:
   collecting a plurality of data relating to said user's activity from a first sensor device;
   generating a default calibration parameter for said user based on user profile data;

generating first activity data by applying said default calibration parameter to said plurality of data;

displaying said first activity data on a display;

collecting a plurality of secondary data relating to said user's activity from a second sensor device;

utilizing said plurality of secondary data to calculate a recommended calibration parameter for measurement of said user's activity;

generating an interactive display comprising an identifier relating to said recommended calibration parameter;

enabling said user to select a current calibration parameter from said display; and calibrating said user's activity data using said user-selected calibration parameter to generate calibrated data.

9. The method of claim 8 wherein the identifier relating to said recommended calibration parameter is a first identifier, wherein the interactive display further includes a second identifier relating to said current calibration parameter, and wherein enabling said user to select a current calibration parameter includes enabling the user to move the first identifier relative to the second identifier.

10. The method of claim 9 wherein the interactive display further includes a scale, wherein said first identifier and said second identifier are simultaneously displayed on said scale, and wherein said first identifier is static relative to said scale, and wherein said second identifier is moveable relative to said scale.

11. The method of claim 10 wherein calculation of the recommended calibration parameter includes determining a ratio of the first activity data to the secondary data.

12. The method of claim 8 further comprising
generating second activity data by applying said current calibration parameter to said plurality of data; and
displaying said second activity data on said interactive display in association with the first activity data.

13. The method of claim 12 wherein the current calibration parameter is the recommended calibration parameter.

14. The method of claim 8, wherein the plurality of secondary data relating to said user's activity comprises global positioning satellite (GPS) data, and wherein said recommended calibration parameter is based on a total distance traveled as determined from said GPS data.

15. The method of claim 8, wherein said user's activity comprises a walking, running, cycling, and/or rowing activity for a distance.

16. A method of adjusting a calibration parameter for measurement of a user's activity, said method comprising:

collecting a first plurality of data relating to a user's activity from at least one first sensor carried by the user during said user's activity;

generating first activity data by applying a current calibration parameter to said first plurality of data;

collecting a second plurality of data relating to said user's activity from at least one second sensor carried by the user during said user's activity;

utilizing said second plurality of data to calculate a recommended calibration parameter for measurement of said user's activity;

displaying on an interactive display said first activity data, a first identifier relating to said current calibration parameter and a second identifier relating to said recommended calibration parameter;

enabling said user to adjust said current calibration parameter from said interactive display; and updating said first activity data on said interactive display based on an adjustment to said current calibration parameter by said user.

17. The method of claim 16 wherein enabling said user to adjust said current calibration parameter from said interactive display includes enabling said user to move said second identifier relative to said first identifier.

18. The method of claim 17 wherein said interactive display includes a scale, wherein said first identifier is moveable relative to said scale and said second identifier is static relative to said scale.

19. The method of claim 16 further comprising generating second activity data based on said second plurality of data and displaying said second activity on said interactive display.

20. The method of claim 19 wherein said first activity data is a first distance and said second activity data is a second distance, wherein the first distance is different than the second distance.

* * * * *